United States Patent
Kim et al.

(10) Patent No.: US 10,952,814 B2
(45) Date of Patent: Mar. 23, 2021

(54) IMAGE PROCESSING DEVICE FOR GENERATING DESIGN IMAGE ON BASIS OF REFERENCE MARKER, AND METHOD THEREFOR

(71) Applicant: DIO CORPORATION, Busan (KR)

(72) Inventors: Jin Chul Kim, Busan (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 221 days.

(21) Appl. No.: 16/097,173

(22) PCT Filed: Mar. 14, 2017

(86) PCT No.: PCT/KR2017/002739
§ 371 (c)(1),
(2) Date: Jan. 25, 2019

(87) PCT Pub. No.: WO2017/188593
PCT Pub. Date: Nov. 2, 2017

(65) Prior Publication Data
US 2019/0151046 A1   May 23, 2019

(30) Foreign Application Priority Data

Apr. 28, 2016 (KR) .................. 10-2016-0052013
Aug. 30, 2016 (KR) .................. 10-2016-0110609
(Continued)

(51) Int. Cl.
*A61C 1/08*     (2006.01)
*G06T 7/33*     (2017.01)
(Continued)

(52) U.S. Cl.
CPC .............. *A61C 1/084* (2013.01); *A61B 5/00* (2013.01); *A61B 6/03* (2013.01); *A61B 6/032* (2013.01);
(Continued)

(58) Field of Classification Search
CPC .......... A61C 1/08; A61C 1/084; A61C 19/04; A61C 8/00; A61C 13/00; A61C 9/0046;
(Continued)

(56) References Cited

U.S. PATENT DOCUMENTS 9,585,730 B2* 3/2017 Kim ..................... A61C 1/082
2003/0186195 A1 10/2003 Comfort et al.
(Continued)

FOREIGN PATENT DOCUMENTS

CN     102014783 A     4/2011
EP     2929854 A2      10/2015
(Continued)

OTHER PUBLICATIONS

Scherer, Michael "Presurgical Implant—Site Assessment and Restorative Driven Digital Planning" Den Clin N Am (2014) (Year: 2014).*
(Continued)

*Primary Examiner* — Kim Y Vu
*Assistant Examiner* — Molly Delaney
(74) *Attorney, Agent, or Firm* — Cantor Colburn LLP

(57) ABSTRACT

The present invention relates to a device and method for processing an image for generating a design image based on a reference marker. A method for processing an image for generating a design image based on a reference marker includes receiving, from at least one external device, a computerized tomography (CT) scan image and a plurality of oral scan images related to a person to be treated who has a plurality of reference markers attached to an inside of an
(Continued)

oral cavity, generating a registered image by registering the images on the basis of locations of the plurality of reference markers detected from the images, determining, on the basis of the registered image, a teeth profile related to the inside of the oral cavity of the person to be treated, and generating a design image related to the inside of the oral cavity on the basis of the teeth profile.

15 Claims, 12 Drawing Sheets

(30) Foreign Application Priority Data

Mar. 6, 2017 (KR) .................. 10-2017-0028469
Mar. 6, 2017 (KR) .................. 10-2017-0028475

(51) Int. Cl.
| | |
|---|---|
| *A61B 6/14* | (2006.01) |
| *A61B 5/00* | (2006.01) |
| *A61C 19/04* | (2006.01) |
| *A61B 6/03* | (2006.01) |
| *A61C 8/00* | (2006.01) |
| *A61C 13/00* | (2006.01) |
| *A61C 9/00* | (2006.01) |

(52) U.S. Cl.
CPC .................. *A61B 6/14* (2013.01); *A61C 1/08* (2013.01); *A61C 8/00* (2013.01); *A61C 9/0046* (2013.01); *A61C 13/00* (2013.01); *A61C 19/04* (2013.01); *G06T 7/33* (2017.01); *G06T 2207/10081* (2013.01); *G06T 2207/30036* (2013.01); *G06T 2207/30204* (2013.01)

(58) Field of Classification Search
CPC .. A61B 5/00; A61B 6/03; A61B 6/032; G06T 2207/10081; G06T 2207/30036; G06T 2207/30204; G06T 7/00; G06T 7/33
See application file for complete search history.

(56) References Cited

U.S. PATENT DOCUMENTS

| | | | |
|---|---|---|---|
| 2009/0042167 A1* | 2/2009 | Van Der Zel | G01J 3/508 |
| | | | 433/215 |
| 2009/0220134 A1 | 9/2009 | Cahill et al. | |
| 2010/0255445 A1 | 10/2010 | Grantes | |
| 2012/0100500 A1* | 4/2012 | Gao | A61C 1/084 |
| | | | 433/72 |
| 2013/0023888 A1 | 1/2013 | Choi et al. | |
| 2015/0025855 A1* | 1/2015 | Fisker | A61C 8/008 |
| | | | 703/1 |
| 2015/0209118 A1 | 7/2015 | Kopelman et al. | |
| 2015/0320520 A1* | 11/2015 | Schulter | A61C 5/77 |
| | | | 433/29 |
| 2016/0354169 A1* | 12/2016 | Suttin | A61C 8/0089 |
| 2017/0071705 A1 | 3/2017 | Kuo | |
| 2020/0170764 A1* | 6/2020 | Schulter | A61C 13/0004 |

FOREIGN PATENT DOCUMENTS

| | | |
|---|---|---|
| JP | 2007-511275 A | 5/2007 |
| JP | 2012-096080 A | 5/2012 |
| JP | 2013-000322 A | 1/2013 |
| KR | 10-2004-0078363 A | 9/2004 |
| KR | 10-0970341 B1 | 7/2010 |
| KR | 10-0977911 B1 | 8/2010 |
| KR | 10-2014-0079557 A | 6/2014 |
| KR | 10-1554157 B1 | 9/2015 |
| KR | 20160027433 A | 3/2016 |
| KR | 10-1608017 B1 | 4/2016 |
| KR | 10-1631256 B1 | 6/2016 |
| RU | 2400178 C1 | 9/2010 |
| WO | 2007-009719 A1 | 1/2007 |
| WO | 2008-083857 A1 | 7/2008 |
| WO | 2008083857 A1 | 7/2008 |

OTHER PUBLICATIONS

ISA/KR, International Search Report dated Jul. 10, 2017 in International Patent Application No. PCT/KR2017/002739, total 4 pages with English translation.
Chinese Office Action for Chinese Application No. 201780026600.7 dated Jun. 30, 2020.
Indian Office Action for Indian Application No. 20187043862 dated Jun. 23, 2020.

\* cited by examiner

IMAGE PROCESSING DEVICE FOR GENERATING DESIGN IMAGE ON BASIS OF REFERENCE MARKER, AND METHOD THEREFOR

RELATED APPLICATIONS

This application is the U.S. National Phase of and claims priority to International Patent Application No. PCT/KR2017/002739, International Filing Date Mar. 14, 2017; which claims benefit of Korean Patent Application No. 10-2016-0052013 filed Apr. 28, 2016, Korean Patent Application No. 10-2016-0110609 filed Aug. 30, 2016, Korean Patent Application No. 10-2017-0028469 filed Mar. 6, 2017, Korean Patent Application No. 10-2017-0028475 filed Mar. 6, 2017; all of which are incorporated herein by reference in their entireties.

TECHNICAL FIELD

The present invention relates to a device and method for processing an image for generating a design image based on a reference marker, and more particularly, to a device and method for processing an image capable of generating a registered image using a computerized tomography (CT) scan image and an oral scan image related to an inside of an oral cavity of a person to be treated to which a reference marker is attached and capable of using the generated registered image to generate a design image.

BACKGROUND ART

Generally, an implant refers to a replacement capable of substituting for a human tissue when an original human tissue is lost, and particularly, refers to implanting an artificial tooth, which is formed using a prosthesis including a fixture, an abutment, and a crown, in a location of an actual tooth.

Implant surgery is performed by forming a borehole in an alveolar bone to place a fixture in the borehole and, when the fixture is fused with the alveolar bone, coupling an abutment and a crown to the fixture. In a dental office, a surgical guide is used for more accurate implant surgery.

Generally, a crown and a surgical guide are manufactured on the basis of an image generated by combining information acquired from a computerized tomography (CT) scan image and information acquired from a three-dimensional oral scan image. In this case, a shape of the crown is designed using an oral scan image which is captured in a state in which a structure is installed inside an oral cavity of a person to be treated and an upper jaw and a lower jaw are occluded.

In the state in which the structure is held inside the oral cavity, since it is not possible to perform an oral scan related to an inner side of teeth, integration occurs with an oral scan image related to an inner side of teeth in a state in which the structure is removed. However, an error occurs in the integration process, and image accuracy is significantly degraded. In addition, in the case of the oral scan image, since it is acquired from information which is scanned by moving an oral scanner along the inside of the oral cavity of the person to be treated, a curvature or the like of the teeth may be distorted and different from the actual inside. Accordingly, there is a problem in that accuracy of the crown and the surgical guide generated using the CT scan image and the oral scan image is degraded.

DISCLOSURE

Technical Problem

Various embodiments of the present invention for solving such problems of the related art are directed to providing a device and method for processing an image for generating a design image based on a reference marker capable of generating a registered image on the basis of a computerized tomography (CT) scan image and an oral scan image.

In addition, various embodiments of the present invention are directed to providing a device and method for processing an image for generating a design image based on a reference marker capable of generating a design image of a structure related to an inside of an oral cavity or a placement location in which an artificial tooth is placed in relation to implant surgery of a person to be treated.

Technical Solution

According to an embodiment of the present invention, a method for processing an image for generating a design image based on a reference marker includes receiving, from at least one external device, a computerized tomography (CT) scan image and a plurality of oral scan images related to a person to be treated who has a plurality of reference markers attached to an inside of an oral cavity, generating a registered image by registering the images on the basis of locations of the plurality of reference markers detected from the images, determining, on the basis of the registered image, a teeth profile related to the inside of the oral cavity of the person to be treated, and generating a design image related to the inside of the oral cavity on the basis of the teeth profile.

Meanwhile, according to an embodiment of the present invention, a device for processing an image for generating a design image based on a reference marker includes a communication unit configured to receive, from at least one external device, a computerized tomography (CT) scan image and a plurality of oral scan images related to a person to be treated who has a plurality of reference markers attached to an inside of an oral cavity, and a processor configured to generate a registered image by registering the received images on the basis of locations of the plurality of reference markers detected from the images and configured to generate a design image of the inside of the oral cavity according to a teeth profile related to the inside of the oral cavity of the person to be treated which is determined on the basis of the registered image.

Advantageous Effects

As described above, according to a device and method for processing an image for generating a design image based on a reference marker of the present invention, a plurality of reference markers are attached to an inside of an oral cavity of a person to be treated or to an occlusion alignment variable piece, a computerized tomography (CT) scan image and an oral scan image related to the inside of the oral cavity are acquired, and a registered image is generated on the basis of the reference markers so that the images can be registered precisely and accurately.

In addition, according to the device and method for processing an image for generating a design image based on a reference marker of the present invention, design images of a crown at a placement location in which an artificial tooth will be placed inside an oral cavity on the basis of a registered image, which shows information on occlusion inside the oral cavity in detail, and a surgical guide for guiding drilling of a borehole for a fixture configured to fix the crown are generated so that a more accurate surgical guide can be manufactured.

MODES OF THE INVENTION

Figure 1:
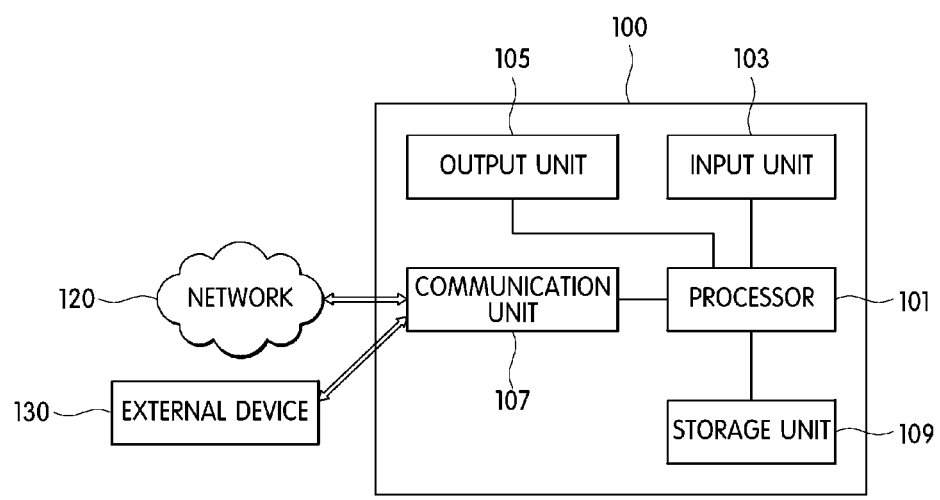
FIG. 1 illustrates elements of an image processing device according to an embodiment of the present invention.

Hereinafter, various embodiments of the present invention will be described in detail with reference to the accompanying drawings. However, parts irrelevant to the description may have been omitted from the drawings for clarity of the description of the present invention. In addition, the same or like elements may be denoted by the same reference numerals throughout.

In various embodiments of the present invention, expressions such as "or" and "at least one" may indicate one of terms listed together or indicate a combination of two or more terms.

Terms used in various embodiments of the present invention are for describing a specific embodiment and should not be interpreted as limiting the present invention. For example, a singular expression may include a plural meaning unless the context clearly indicates otherwise.

A device according to various embodiments of the present invention relates to a device for processing an image (hereinafter, an image processing device) for manufacturing a crown or a medical surgical guide for implant and an operation method thereof. In this case, the image processing device may perform image processing of a structure by detecting a reference marker attached to an inside of an oral cavity of a person to be treated from an image.

Here, implant surgery includes a process in which a borehole is formed at an implant placement location using a drill and a fixture is placed in the borehole. In this case, it is preferable that the surgical guide be understood as a device configured to guide a position and a direction during drilling of the borehole or engagement of the fixture.

Here, it is preferable that the inside of the oral cavity of the person to be treated be understood to have a meaning that encompasses teeth including a natural tooth or an artificial tooth, gums, an alveolar bone, a palate, and the like. In addition, it is preferable that the implant placement location be understood as a location where the person to be treated wants the implant surgery to be performed of a portion from which a tooth which has lost its function has been extracted or a portion which requires tooth extraction.

FIG. 1 illustrates elements of an image processing device 100 according to an embodiment of the present invention. The image processing device 100 includes at least one element among a processor 101, an input unit 103, an output unit 105, a communication unit 107, and a storage unit 109.

The processor 101 may receive data from the other elements listed above (e.g., the input unit 103, the output unit 105, the communication unit 107, and the storage unit 109), check the received data, and process the checked data.

According to an embodiment, the processor 101 receives an image which is input via the input unit 103. Alternatively, the processor 101 receives an image from at least one external device 130 via the communication unit 107.

A computerized tomography (CT) scan image or an oral scan image related to an inside of an oral cavity of a person on which implant surgery will be performed may be provided as an image that the image processing device 100 receives.

Here, a CT scan image 200 is an image scanned by a CT device using radiation. That is, the CT scan image may show distributions of internal tissues and bone density information related to a crown, a root, an alveolar bone, and the like inside the oral cavity based on a transmission rate of radiation. A reference marker may be clearly displayed in the CT scan image even if scattering of light occurs due to a metal prosthesis during scanning.

In addition, the oral scan image is an image scanned by an oral scanner (e.g., an oral-scanning device). That is, the oral scan image shows an overall shape related to an outer shape of gums, which are soft tissues, that is difficult to be acquired by CT as well as an outer shape of crowns of teeth.

Further, the oral scan image may include a separation oral scan image in a state in which an upper jaw and a lower jaw of the person to be treated are separated and an occlusion oral scan image in a state in which the upper jaw and the lower jaw are occluded.

Here, the separation oral scan image and the occlusion oral scan image may be provided as images that result from performing oral scanning on the upper jaw and the lower jaw. The processor 101 may combine the oral scan images to generate a single oral scan image including the upper jaw and the lower jaw.

In addition, the occlusion oral scan image may be provided as an oral scan image that results from scanning a structure of the inside of the oral cavity of the person to be treated in a state in which an occlusion alignment variable piece, which is disposed to correspond to an occlusion height while the upper jaw and the lower jaw of the person to be treated are closed, is installed. The processor 101 may receive at least one image of an outer shape of the occlusion alignment variable piece which is separated from the oral cavity of the person to be treated after scanning.

Here, the occlusion alignment variable piece may be formed to include a body portion and an occlusion base. The body portion includes a shape-matching groove portion whose shape is matched to that of at least a portion of a crown or gums inside the oral cavity of the person to be treated. In addition, in the body portion, the occlusion base may be formed at a side corresponding to the shape-matching groove portion, and a hardening impression resin may be additionally formed on an upper surface of the occlusion base. During installation of the occlusion alignment variable piece, the shape of the shape-matching groove portion is matched to that of an outer surface of a tooth placement target portion (or tooth target portion) of the person to be treated. Here, at least one reference marker may be formed at the body portion or the occlusion base of the occlusion alignment variable piece.

The occlusion base of the occlusion alignment variable piece installed inside the oral cavity of the person to be treated is installed so that opposing teeth are seated on the upper surface of the occlusion base during occlusion of the upper jaw and the lower jaw. In this case, a masticatory groove whose shape is matched with that of ends of the opposing teeth are formed in the upper surface of the occlusion base. Here, the shape of the masticatory groove formed in the occlusion alignment variable piece may serve as a guide for determining an accurate occlusion height of the opposing teeth and determining a shape of a crown.

The processor 101 may acquire images of a tooth placement target portion-side outer surface of the person to be treated and an opposing teeth-side outer surface corresponding thereto on the basis of the received occlusion oral scan image or the separation oral scan image. In addition, the processor 101 may check an occlusion image related to masticatory motion of the upper jaw and the lower jaw on the basis of the occlusion oral scan image and the separation oral scan image.

In this case, at least one reference marker has been attached to the inside of the oral cavity of the person to be treated of which an image is scanned. Therefore, the at least one reference marker attached to the inside of the oral cavity of the person to be treated may be displayed in the CT scan image and the oral scan image.

Here, the reference marker may be formed of a resin identifier including a radiopaque resin structure and a reinforcing adhesive (or adhesive layer) for attaching the resin structure to the inside of the oral cavity. That is, the reference marker includes a radiopaque material. Therefore, the reference marker may be clearly displayed even in the CT scan image using radiation as well as the oral scan image which results from scanning a surface inside the oral cavity.

The reference marker may be formed at a plurality of sites along a surface of a tooth, gums, and a metal prosthesis inside the oral cavity of the person to be treated. In addition, a plurality of reference markers may be densely formed only within a designated area which is adjacent to an implant placement location.

The reference marker attached to the inside of the oral cavity of the person to be treated may have a recessed portion formed therein during a generation process. The formed recessed portion may be displayed to be darker than its surroundings according to a density, an amount of reflected light, and the like in the oral scan image or the CT scan image. In this way, the processor 101 may detect a reference marker displayed in an image by detecting a recessed portion in an oral scan image and a CT scan image, or images used in an image registration process. In addition, in a case in which a reference marker is detected from an oral scan image, the processor 101 may also detect a reference marker formed at the occlusion alignment variable piece.

The processor 101 checks reference markers at the same location using a reference marker displayed in each image. The processor 101 registers a CT scan image and an oral scan image on the basis of the reference markers at the same location which have been detected from each image.

According to an embodiment, the processor 101 determines at least some of the reference markers included in each image as registration points for registering the images. The processor 101 matches reference markers related to the same location among the determined registration points so that the reference markers are made to correspond to a single point.

Here, the processor 101 may perform determination on the basis of a reference image, e.g., a CT scan image. The processor 101 may perform determination so that reference markers are made to correspond to a single point (or match) when a reference marker in an oral scan image overlaps with a reference marker displayed in a CT scan image or when the reference markers are disposed relative to each other within a designated error range.

The processor 101 may perform matching of reference markers while the upper jaw and the lower jaw in the structure of the oral cavity of the person to be treated displayed in the images are separated. Then, the processor 101 may perform registration of the matched images.

In performing image registration, the processor 101 may perform image correction when reference markers at the same location included in each image are not matched to a single point. Here, the image correction may refer to controlling at least some of a proportion, a magnification, and a direction of an image and the arrangement and size of teeth. In addition, the image correction may refer to distorting or moving a reference marker and a designated surrounding area or, as described above, controlling at least some of the proportion, the magnification, and the direction.

According to an embodiment, the processor 101 may confirm that two or more reference markers at the same location are matched to a single point in a state in which a CT scan image and an oral scan image overlap with each other. The processor 101 may perform, on the basis of the corresponding two or more reference markers as reference registration points, image correction so that the remaining reference markers which are not matched to a single point are made to correspond to each other.

Here, the image correction may refer to correcting a curvature of teeth displayed in a CT scan image or an oral scan image.

The processor 101 generates a registered image by registering a CT scan image and an oral scan image. According to an embodiment, the processor 101 may generate a single registered image by registering a CT scan image and an oral scan image while reference markers related to the same location included in the images correspond to a single point. The processor 101 may generate a teeth profile of the person to be treated using the registered image. Here, the teeth profile may be defined as an area extending from a curve of teeth corresponding to a tooth placement target portion toward a tongue side or a cheek side of the person to be treated. In addition, the tooth placement target portion may be defined to encompass teeth 30 of the person to be treated, or a metal prosthesis, an artificial tooth, and an implant placement location 3 in which an artificial tooth will be placed.

The teeth profile includes detailed information on the structure of the oral cavity of the person to be treated based on a registered image and reference marker included in the image. For example, the teeth profile may include information related to teeth, crowns, and gums around an implant placement location and information related to an alveolar bone and roots inside the gums. In addition, such images may be provided as three-dimensional images.

Here, the teeth profile may be generated on the basis of a registered image as described above, but may also be generated by performing a re-generation or an update using a pre-generated teeth profile related to the person to be treated. For example, the pre-generated teeth profile related to the person to be treated may have been generated using a general oral cavity structure image, a CT-scan oral cavity structure image, or an oral-scan oral cavity structure image of the person.

In this case, in the pre-generated teeth profile, a location of a reference marker formed inside the oral cavity of the person to be treated may be displayed in an image, or coordinates may be set in relation to at least one reference marker. The processor 101 may update the pre-generated teeth profile on the basis of a registered image.

The processor 101 may design a shape of a prosthesis to be placed in the tooth placement target portion of the person to be treated on the basis of the teeth profile. For example, the processor 101 may arrange a fixture, an abutment, or a crown which is placed in each implant placement location on the basis of the teeth profile.

The processor 101 may determine a shape of a crown to be placed in the implant placement location of the person to be treated on the basis of at least some of the separation oral scan image, the occlusion oral scan image, and/or the image of the occlusion alignment variable piece in which the masticatory groove is formed, and the registered image generated by registering the images.

In addition, the processor 101 is not limited to determining the shape of the crown to be placed in the implant placement location using the teeth profile as described above, and various other embodiments are possible. For example, the processor 101 may determine the shape of the crown on the basis of the image of the occlusion alignment variable piece as well as the separation oral scan image, the occlusion oral scan image, and the registered image using the images. According to an embodiment, the image of the occlusion alignment variable piece may include a masticatory groove of opposing teeth corresponding to the implant placement location while the upper jaw and the lower jaw of the person to be treated are occluded. The processor 101 may determine an occlusion height on the basis of the shape of the masticatory groove and determine the height and shape of the crown to be placed in the implant placement location.

According to an embodiment, the processor 101 may arrange the generated shape of the crown at the corresponding implant placement location of the registered image. The processor 101 may check occlusion between the arranged shape of the crown and the opposing teeth and partially modify the shape of the crown or precisely control a location at which the crown is placed in the implant placement location.

The processor 101 generates a design image of a structure related to implant surgery for the person to be treated on the basis of the registered image or teeth profile generated as described above. According to an embodiment, the processor 101 may generate a design image related to a surgical guide or a crown, and the design image may include a three-dimensional design drawing.

Here, the surgical guide may be provided as a structure for guiding drilling for insertion of a fixture during implant surgery. The surgical guide may include at least one guide hole configured to guide drilling.

According to an embodiment, the image processing device 100 may determine a fixing location of the fixture on the basis of the teeth profile in the registered image in which the arrangement of the crown has been determined as described above.

For example, the fixing location of the fixture may be determined on the basis of information such as a direction and a depth in which the fixture is placed in the alveolar bone of the person to be treated. During the implant surgery, when the shape of the crown or the location at which the crown is fixed is changed, the fixing location of the fixture, which is a foundation of the crown, may also be changed. Therefore, the processor 101 may precisely determine the fixing location of the fixture according to the shape and location of the crown determined as described above.

In the design image of the surgical guide generated by the processor 101, the shape of the structure is generated to match the shape of the outer surface of the gums at the implant placement location. Here, the shape of the structure may include a guide hole so that drilling may be accurately performed at the determined fixing location of the fixture, and a mounting portion on which a drill is mounted may be formed at one side of the guide hole.

In addition, instead of only taking the crown into consideration in determining the fixing location of the fixture as described above, a shape of an abutment which is coupled to the crown or the fixture may also be taken into consideration.

The processor 101 performs three-dimensional printing by sending at least one of the generated design image of the crown and the design image of the surgical guide to the external device 130 via the communication unit.

The input unit 103 is an element for receiving information and/or a control command for processing an image received via the communication unit 107, e.g., a CT scan image or an oral scan image. For example, the input unit 103 may include at least one of a keyboard, a keypad, a touchscreen, at least one button, and a microphone.

The output unit 105 outputs data processed by the processor 101, e.g., the entire input CT scan image and oral scan image or a partial area thereof. According to an embodiment, the output unit 105 may include at least one of a display and a speaker.

When the output unit 105 is provided as a display, data sent to the display via the processor 101 may be displayed through a graphic user interface. In various embodiments of the present invention, the image processing device 100 may perform an operation of displaying or outputting an image by the output unit 105.

In addition, when the output unit 105 is provided as a speaker, data sent to the speaker via the processor 101 may be output through an audio.

The communication unit 107 may connect the image processing device 100 to an external communication network. For example, the communication unit 107 may be connected to a network 120 through wireless communication or wired communication and/or communicate with the external device 130. According to an embodiment of the present invention, the network 120 may be a telecommunications network.

The external device 130 is illustrated as performing direct communication with the image processing device 100 via the communication unit 107, but embodiments are not limited thereto, and it is apparent that the external device 130 may communicate with the image processing device 100 via the network 120.

The external device 130 may be connected to the image processing device 100 through wireless communication and/or wired communication and may be provided as the same or like device as the image processing device 100. In addition, the external device 130 may be configured with the image processing device 100, one element thereof, or a combination of more than one elements thereof.

According to an embodiment, the external device 130 may be provided as an image acquisition device which performs a CT scan or an oral scan of an inside of an oral cavity of a person to be treated as described above. In addition, the external device 130 may be provided as a 3D printer which generates a surgical guide by three-dimensionally printing a generated design image.

The storage unit 109 may store commands and/or data received from the processor 101 or other elements or generated by the processor 101 or the other elements.

Further, the storage unit 109 may store data input via the input unit 103 and/or the communication unit 107, e.g., a CT scan image or an oral scan image received from the external device 130. In addition, the storage unit 109 may store at least some of images processed by the processor 101 and a generated registered image.

Hereinafter, a process in which the image processing device 100 generates a registered image using a reference marker will be described with reference to FIGS. 2 to 6. Then, a process in which the image processing device 100 generates a design image of a structure related to an inside of an oral cavity on the basis of the registered image will be described.

In the following description, various embodiments of the present invention will be described as being performed by the image processing device 100. As described above, the operations of the image processing device 100 may be performed by at least one of the processor 101, the input unit 103, the output unit 105, the communication unit 107, and the storage unit 109 or a combination of two or more thereof.

Figure 2:
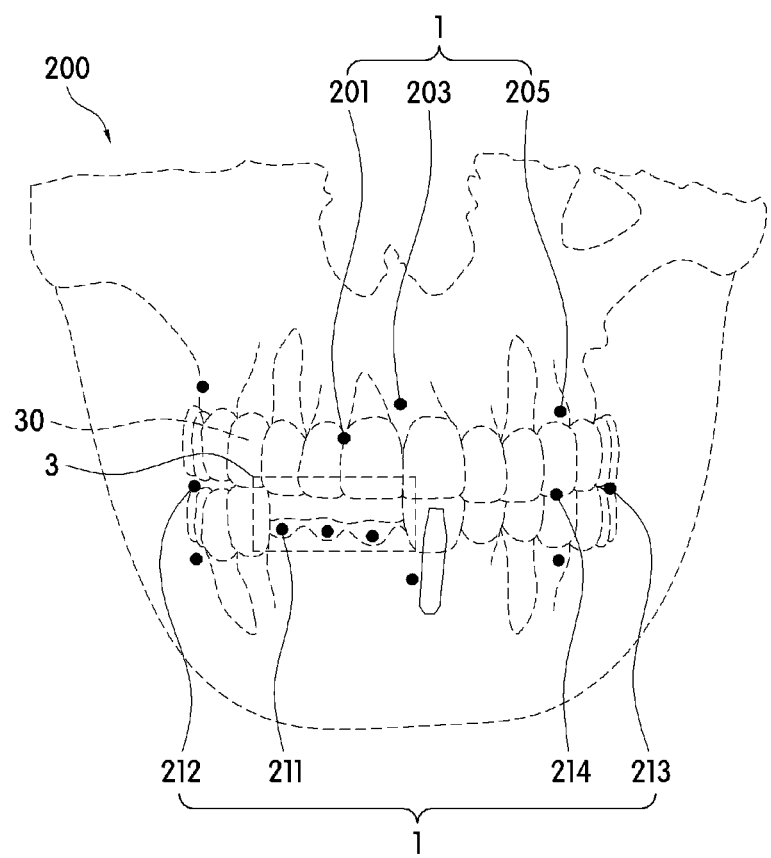
FIG. 2 is a computerized tomography (CT) scan image which is input to the image processing apparatus according to an embodiment of the present invention.
Figure 3:
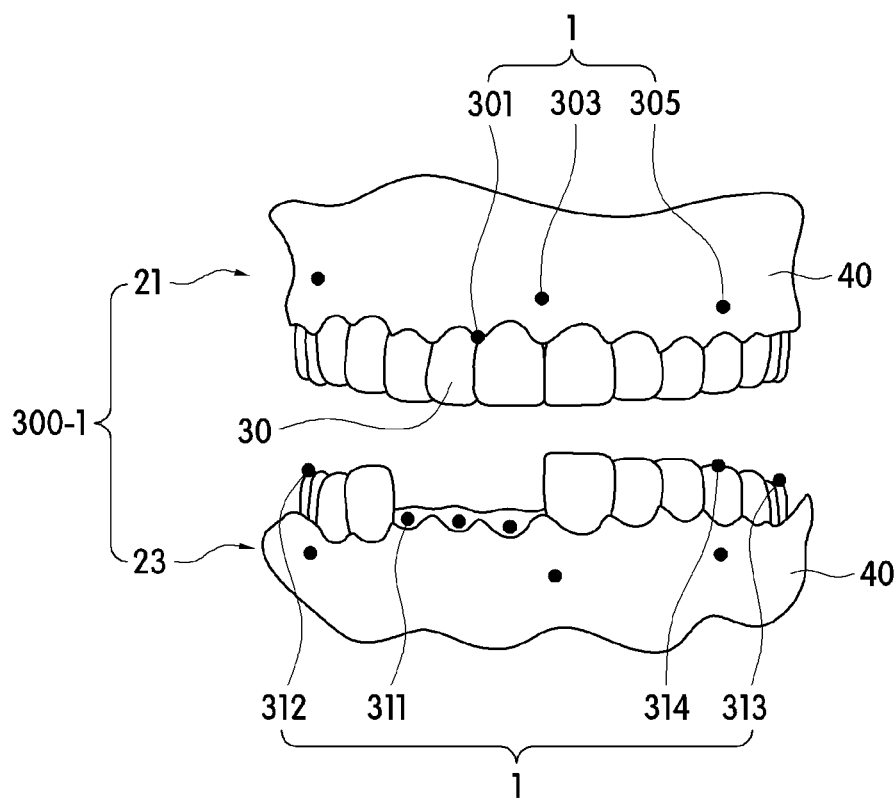
FIG. 3 is a separation oral scan image which is input to the image processing device according to an embodiment of the present invention.

FIG. 2 is a CT scan image which is input to the image processing apparatus according to an embodiment of the present invention. FIG. 3 is a separation oral scan image 300-1 which is input to the image processing device according to an embodiment of the present invention.

The image processing device 100 detects reference markers 1 displayed on each of the CT scan image 200 and the separation oral scan image 300-1. In this case, a reference marker of the separation oral scan image 300-1, which matches a reference marker displayed in the CT scan image 200, is acquired from a reference marker that is attached at substantially the same location.

For example, a reference marker 201 displayed in the CT scan image 200 and a reference marker 301 displayed in the separation oral scan image 300-1 may be scanned shapes of the same reference marker formed inside the oral cavity of the person to be treated. Likewise, reference markers 203, 205, 211, 212, 213, and 214 of the CT scan image 200 and reference markers 303, 305, 311, 312, 313, and 314 of the separation oral scan image 300-1, which match one another, and other matching reference markers in the images may be scanned shapes of the same reference markers formed inside the oral cavity of the person to be treated.

The image processing device 100 determines two or more reference markers 1 among the matching reference markers 1 related to the same location as registration points which become standards of image registration.

Referring to FIGS. 2 and 3, the image processing device 100 may determine the reference markers 201, 203, and 211 of the CT scan image 200 and the reference markers 301, 303, and 311 of the separation oral scan image 300-1, which match the reference markers 201, 203, and 211 of the CT scan image 200, as registration points.

In this case, when a pair of matching reference markers related to each image constitute one set, two or more reference marker sets may be determined as the registration points which become standards of image registration. For example, the processor 101 may determine two or more reference marker sets among the set of reference markers 201 and 301, the set of reference markers 203 and 303, and the set of reference markers 205 and 305 as the registration points. Here, the reference marker sets determined as the registration points may be determined as reference markers which are located within a designated distance or in the proximity of a designated location.

As described above, the image processing device 100 checks, on the basis of two or more reference marker sets which match in a state in which the images are partially not distorted or changed, whether locations of the remaining reference markers match.

When the remaining reference markers match, the image processing device 100 registers the images and generates a registered image. On the other hand, when at least some of the remaining reference markers do not match, the image processing device 100 corrects at least one image so that the reference markers are matched to a single point. The CT scan image or the separation oral scan image input to the image processing device 100 may be provided as a plurality of images which include a partial area related to the inside of the oral cavity of the person to be treated.

Particularly, the separation oral scan image 300-1 is formed by combining a plurality of consecutive images which are scanned by moving an oral scanner. In this case, in the case of an edentulous patient, it is difficult to determine a combination reference point between consecutive images due to mobile surfaces of gums.

In generating a single CT scan image or a single separation oral scan image by combining a plurality of input images, as described above, the image processing device 100 combines the images on the basis of the reference markers 1 displayed in the images so that an error may be minimized in image matching.

That is, the registration points, which are determined using sets of the plurality of reference markers 1, may clearly propose combination reference points between images. The image processing device 100 performs image registration using the reference markers 1 which are determined as registration points in each image so that accuracy of a result of performing image registration using the CT scan image or the separation oral scan image is improved.

Further, in registering the images, the image processing device 100 may additionally use various pieces of detected information on the reference markers 1 and the inside of the oral cavity to match and register the images.

For example, the image processing device 100 may detect, from the CT scan image 200, factors inside the oral cavity such as the shape or form of a crown, a root, and a tooth extraction portion and a structure of teeth. In addition, the image processing device 100 may detect, from the separation oral scan image 300-1, factors inside the oral cavity such as the shape or form of a crown, gums, and a tooth extraction portion and a structure of teeth.

By matching the detected factors inside the oral cavity, the image processing device 100 may register the CT scan image 200 and the separation oral scan image 300-1. In this case, the image processing device 100 may compare similar shapes and forms which are not common to the same location. For example, among the detected factors, crown and alveolar bone areas in the CT scan image 200 and gum areas in the separation oral scan image 300-1 display shapes with different characteristics at the same location. However, the image processing device 100 may compare and match the images on the basis of the shape and form of factors (e.g., crowns) common to such areas.

As described above, the image processing device 100 may compare factors inside the oral cavity which are detected from each of the CT scan image 200 and the separation oral scan image 300-1 and determine a registration location on the basis of factors which are determined as being the same or similar.

In performing image registration, the image processing device 100 may acquire comprehensive information by matching information on a root and an alveolar bone connected to a crown in the CT scan image 200 with information on gums bonded a root and an alveolar bone in the separation oral scan image 300-1.

Figure 9:
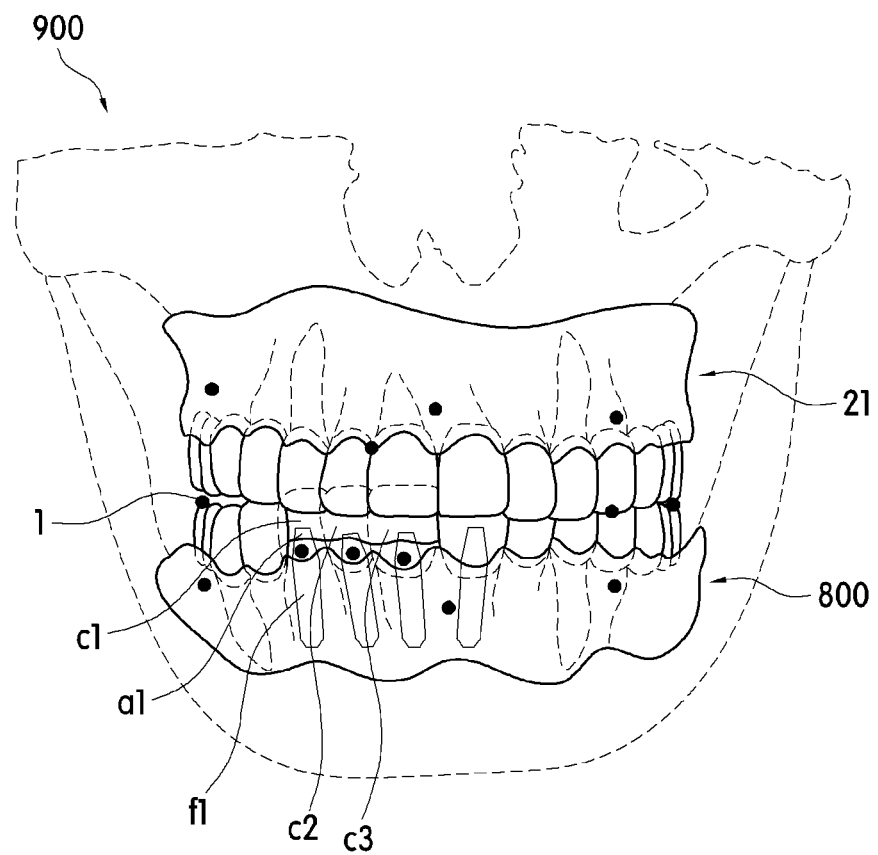
FIG. 9 illustrates a registered image in which a CT scan image and an oral scan image are registered using the image processing device according to an embodiment of the present invention.

As described above, the image processing device 100 may precisely determine a registration location by comparing the determined registration points and the elements displayed in the images and generate a registered image 900 as illustrated in FIG. 9 by registering the images at the determined location.

According to various embodiments, the image processing device 100 may match the reference markers by separating the upper jaw and the lower jaw in the structure inside the oral cavity of the person to be treated that is displayed in the separation oral scan image and the CT scan image.

For example, during scanning of the CT scan image 200 and the separation oral scan image 300-1, a difference may occur in a degree to which a mouth of the person to be treated is open according to a scanning situation. Therefore, a difference may occur in terms of a state in which the upper jaw and the lower jaw are separated between the structures inside the oral cavity of the person to be treated displayed in the CT scan image 200 and the separation oral scan image 300-1.

When the CT scan image and the separation oral scan image, which differ in terms of the state in which the upper jaw and the lower jaw are separated, are registered without a correction, since registration points do not correspond to each other, serious distortion may occur in an area in which the structure of the inside of the oral cavity of the person to be treated is displayed in the generated registered image 900. Therefore, in order to minimize such distortion, the image processing device 100 may perform an operation in which a gap generated between the upper jaw and the lower jaw in the CT scan image 200 and the separation oral scan image 300-1 is corrected.

Figure 4:
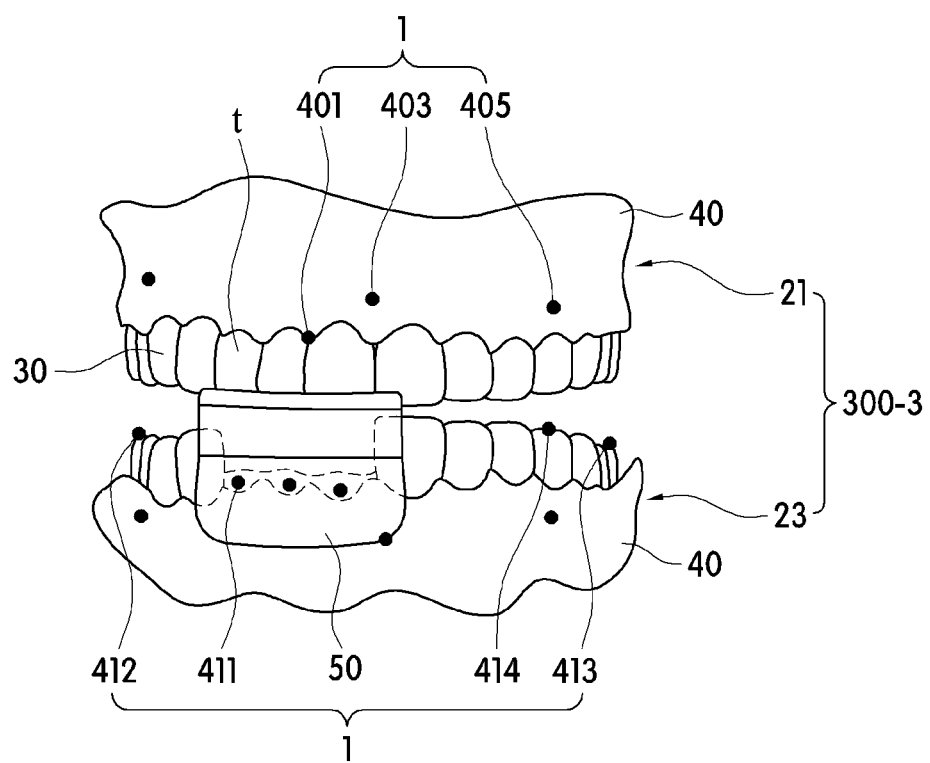
FIG. 4 is an occlusion oral scan image which is input to the image processing device according to an embodiment of the present invention.

In this case, the image processing device 100 separates the structure of the inside of the oral cavity of the person to be treated which is displayed in the separation oral scan image 300-1 into a maxillary shape 21 and a mandibular shape 23 as illustrated in FIGS. 3 and 4 to compare the structure of the inside of the oral cavity with the structure of the inside of the oral cavity in the CT scan image. Here, "shape" as in the maxillary shape or the mandibular shape may also refer to an image including the shape.

The image processing device 100 may control the maxillary shape 21 or the mandibular shape 23 of the separation oral scan image 300-1 to perform matching of the reference markers 1 with the CT scan image 200. For example, the image processing device 100 may move the maxillary shape 21 or the mandibular shape 23 to perform matching of the reference markers 1 with the CT scan image 200. In this case, the image processing device 100 may correct at least one of the maxillary shape 21 or the mandibular shape 23.

The image processing device 100 performs matching of the reference markers 1 and registration of the images and generates a teeth profile on the basis of the generated registered image. Then, the image processing device 100 determines the shape of the crown to be placed in the implant placement location 3 on the basis of the generated profile.

The image processing device 100 may determine the shape of the crown on the basis of occlusion between the upper jaw and the lower jaw of the person to be treated and the shape of the opposing teeth occluded with the crown. In this case, in order to design the shape of the crown which allows the opposing teeth to be precisely occluded while the upper jaw and the lower jaw of the person to be treated are occluded, an oral scan image in a state in which the upper jaw and the lower jaw of the person to be treated are occluded is required. Hereinafter, various embodiments in which the image processing device 100 processes an oral scan image and an image of an occlusion alignment variable piece will be described with reference to FIGS. 4 to 6.

Figure 5:
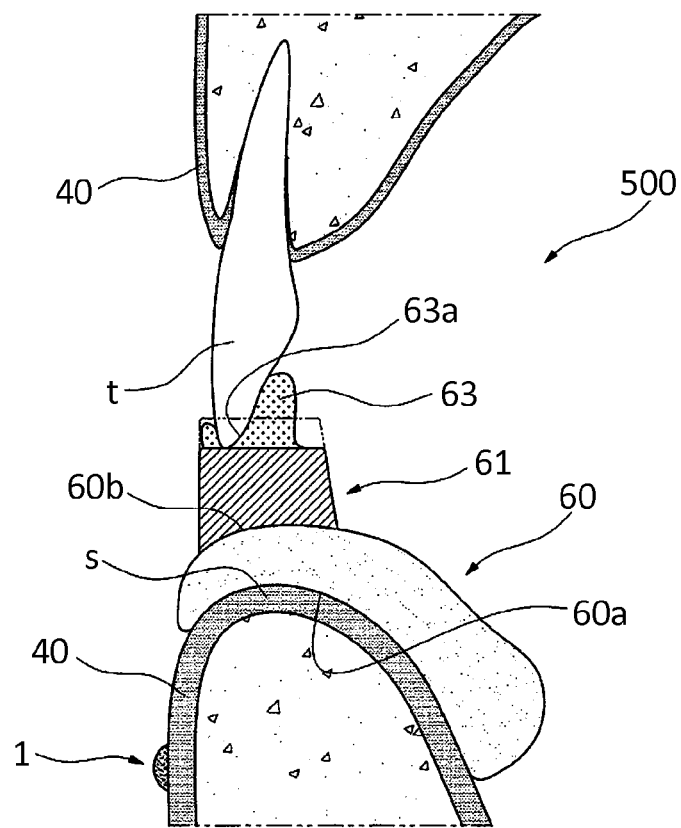
FIG. 5 is a cross-sectional view of an oral scan image which is input to the image processing device according to an embodiment of the present invention.
Figure 6:
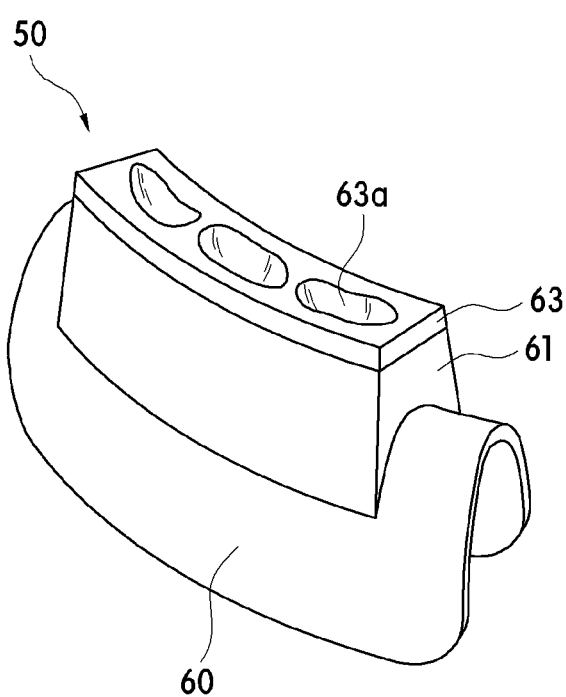
FIG. 6 is an image of an occlusion alignment variable piece which is input to the image processing device according to an embodiment of the present invention.

FIG. 4 is an occlusion oral scan image 300-3 which is input to the image processing device 100 according to an embodiment of the present invention. FIG. 5 is a cross-sectional view of the occlusion oral scan image 300-3 which is input to the image processing device 100 according to an embodiment of the present invention. FIG. 6 is an image of an occlusion alignment variable piece 50 which is input to the image processing device 100 according to an embodiment of the present invention.

As described above, the occlusion oral scan image 300-3 may be provided as an oral scan image which is scanned in a state in which the occlusion alignment variable piece 50 is installed (or mounted) inside an oral cavity of a person to be treated. The occlusion oral scan image 300-3 may be provided as an oral scan image in a state in which an outer surface at the implant placement location 3-side and an outer surface at the opposing teeth t-side corresponding thereto are occluded.

According to an embodiment, as illustrated in FIGS. 4 and 5, an occlusion base 61 may be stacked on a body portion 60 in the occlusion alignment variable piece 50.

According to an embodiment, the body portion 60 may be formed of a thermoplastic resin material. For example, the body portion 60 may include a thermoplastic synthetic resin material selected from the group consisting of polyester, polyurethane, polycaprolactone, and a mixture thereof.

Here, the thermoplastic synthetic resin material may be defined as a material which is a solid whose elasticity and denaturation are minimized at a preset temperature or lower but, when processed at a preset temperature or higher, is softened and elastically deformed due to a pressing operation (e.g., kneading by hand) by an operator.

Accordingly, a shape-matching groove portion 60a whose shape is matched to that of the inside of the oral cavity, e.g., a crown, gums, and/or gums at the implant placement location 3, after being processed to the preset temperature or higher, softened, and then pressed and bonded inside the oral cavity of the person to be treated is formed in the body portion 60. In this case, at an opposite side of one side of the body portion 60 at which the shape-matching groove portion 60a is formed, the occlusion base 61 which is occluded with the opposing teeth t during bonding of the occlusion alignment variable piece 50 is disposed to be stacked.

According to various embodiments, the body portion 60 of the occlusion alignment variable piece 50 may be formed in a bar or spherical shape, an arch shape corresponding to a dental arch, or an atypical shape, and a required amount thereof may be torn out and then press-bonded to the inside of the oral cavity of the person to be treated. That is, the body portion 60 may be formed in various forms as long as it is easy to press and attach the form to the inside of the oral cavity of the person to be treated.

Further, the thermoplastic synthetic resin, which is a material of the body portion 60, may also be disposed in the form in which it is filled in a syringe. For example, if the syringe itself is processed to a preset temperature or higher, the thermoplastic synthetic resin filled therein is softened. Then, when the syringe is pressed so that the material filled therein is pressed in a state in which it is discharged to the inside of the oral cavity of the person to be treated, the body portion 60 whose shape is matched with that of the inside of the oral cavity may be formed.

In this case, various devices may be used in order to elevate the temperature of the body portion formed of the thermoplastic synthetic resin material to a preset temperature or higher. However, hot water whose temperature has been elevated may be used to facilitate preparation and operation. That is, when the body portion 60 is dipped in the hot water whose temperature has been elevated to a preset temperature or higher, the body portion 60 may be softened due to the temperature of the hot water.

Here, the hot water may have a temperature in the range of 45 to 70° C., and the temperature of the body portion 60 dipped in the above-described hot water may be elevated to a temperature lower than that of the hot water while the body portion 60 is softened. Accordingly, even when the softened body portion 60 is directly press-bonded to the inside of the oral cavity, burn hazard and pain and injury due to high temperature of the person to be treated may be prevented. In this way, since the thermoplastic synthetic resin may be directly press-bonded to the inside of the oral cavity of the person to be treated in place of a resin material which is heated to a high temperature and causes a burn hazard in a conventional polymerization process, safety and convenience of surgery may be significantly improved.

In addition, the body portion 60 may be promptly hardened while being press-bonded to the inside of the oral cavity and manufactured as the occlusion alignment variable piece 50. Accordingly, since the body portion 60 may be promptly separated while the shape-matching groove portion 60a, in which the shape of the inside of the oral cavity of the person to be treated is reversed, is formed, a standby time of the person to be treated may be significantly shortened during manufacture of the occlusion alignment variable piece 50 and inconvenience may be minimized. Further, for prompter hardening, washing water or air may be sprayed using a dental washer to rapidly cool the body portion 60.

Further, the occlusion alignment variable piece 50 may be promptly manufactured using a method in which the body portion 60 is directly press-bonded to the inside of the oral cavity adjacent to a tooth placement target portion s. In this way, since a conventional complicated process in which an occlusion guide means is manufactured by performing impression taking and manufacturing a plaster cast is omitted, a duration and cost of implant surgery may be significantly shortened and reduced.

In addition, since, even if the occlusion alignment variable piece 50 is manufactured somewhat inaccurately, the occlusion alignment variable piece 50 is re-softened when temperature thereof is elevated, a repair work may be performed promptly and conveniently, and it is economically feasible since a separate material is not required for reworking. The occlusion alignment variable piece 50 generated as described above is installed at the implant placement location 3 as illustrated in FIG. 4, and the upper jaw and the lower jaw are occluded. Then, a thickness of the occlusion base 61 may be formed in a suitable occlusion height according to mastication sensitivity felt by the person to be treated. In this case, the occlusion base 61 may be formed of a material, such as paraffin or wax, whose form is easy to be changed by a pressing force or a cutting force while a preset form is maintained, so that selective adjustment of the thickness of the occlusion base 61 according to the mastication sensitivity of the person to be treated is facilitated.

According to an embodiment, when the upper jaw and the lower jaw are occluded in a state in which the occlusion alignment variable piece 50 is installed, a mastication mark corresponding to ends of the opposing teeth t is formed at an upper surface of the occlusion base 61. Then, the occlusion height may be set by adjusting the thickness of the occlusion base 61 to an extent that the person to be treated feels comfortable corresponding to a depth of the formed mastication mark.

Accordingly, even in the case of a patient whose surrounding teeth are mostly lost, since the occlusion alignment variable piece 50 which is adjusted to an optimal occlusion height is provided to the person to be treated, occlusion between the upper jaw and the lower jaw may be guided to a substantially accurate occlusion height. The image processing device 100 may calculate an accurate vertical dimension value from the occlusion oral scan image 300-3 acquired by performing oral scanning of such an occlusion state. In this way, in the image processing device 100, the preciseness and reliability of the designed crown and surgical guide may be significantly improved.

In this case, applying a hardening alignment impression material 63, on which the mastication mark of the opposing teeth t is displayed, on the upper surface of the occlusion base 61 of the occlusion alignment variable piece 50 so that an occlusion location with the opposing teeth t is guided may be further included.

In this case, when the occlusion alignment variable piece 50, in which impression resin is applied on the upper surface of the occlusion base 61, is installed in the oral cavity of the person to be treated, and the upper jaw and the lower jaw are occluded, the mastication mark of the opposing teeth t may be formed. Referring to FIG. 6, the mastication mark may be formed as a mastication groove 63a in the alignment impression material 63 and/or the occlusion base 61. Accordingly, when the occlusion alignment variable piece 50 is installed during oral scanning, an accurate occlusion location may be determined by the ends of the opposing teeth t being constrained to the mastication groove 63a.

The image processing device 100 may perform an operation that is the same as or similar to the operation processed on the separation oral scan image 300-1 on the occlusion oral scan image 300-3 which is scanned while the occlusion alignment variable piece 50 is installed as described above. For example, the image processing device 100 may detect reference markers included in the occlusion oral scan image 300-3.

The image processing device 100 may match reference markers of the occlusion oral scan image 300-3 that respectively match the reference markers 1 of the separation oral scan image 300-1. For example, the image processing device 100 may match reference markers, which are the same as two or more designated reference markers among the reference markers 301, 303, 305, 311, 312, 313, and 314 displayed on the maxillary shape and the mandibular shape in the separation oral scan image 300-1, among reference markers 401, 403, 405, 411, 412, 413, and 414 in the occlusion oral scan image 303-3. For example, the image processing device 100 may arrange the reference markers, which are confirmed to be the same, to be aligned by causing locations of the reference markers to correspond to each other.

Further, in addition to comparing the reference markers, the image processing device 100 may also compare common portions in the oral scan images 300-1 and 300-3 and arrange the images to be aligned. Here, the common portions of the images 300-1 and 300-3 may be defined as portions with almost no mobility such as crowns excluding a flexible tissue such as gums.

As described above, the image processing device 100 may arrange the oral scan images 300-1 and 300-3 to be aligned by separating the maxillary shape 21 and the mandibular shape 23 included in the oral scan images 300-1 and 300-3. In this case, the image processing device 100 may align the maxillary shape and the mandibular shape of the separation oral scan image 300-1 to correspond to the maxillary shape and the mandibular shape of the occlusion oral scan image 300-3 and may remove the occlusion oral scan image 300-3 or the occlusion alignment variable piece 50.

That is, the image processing device 100 may acquire oral scan images of the inside of that oral cavity which are aligned to correspond to an occlusion height of the upper jaw and the lower jaw of the person to be treated and in which substantial shapes of outer surfaces of the upper jaw and the lower jaw are three-dimensionally displayed.

By acquiring the oral scan images of the inside of the oral cavity as described above, images of a portion which is difficult to be checked while the occlusion alignment variable piece 50 is installed inside the oral cavity of the person to be treated, for example, a portion covered by the occlusion alignment variable piece 50, and an inner surface of teeth may be easily checked.

In addition, the image processing device 100 may change a curvature of teeth of a portion of the structure of the inside of the oral cavity of the person to be treated which is displayed in the CT scan image 200 and an oral scan image.

For example, the oral scan image 300-1 is acquired by combining images which are consecutively scanned by an oral scanner which is moved along the inside of the oral cavity of the person to be treated. Therefore, a curvature of teeth shown in the oral scan image 300-1 may be distorted and differ from an actual curvature of teeth inside the oral cavity. On the other hand, in the CT scan image 200, although information on soft tissues such as gums is not clearly displayed, a curvature of teeth is substantially accurately shown.

When image registration is performed using the oral scan image in which distortion has occurred from the actual curvature of teeth inside the oral cavity of the person to be treated, a registered image in which an area in which distortion has occurred is twisted or distortion is occurred throughout an entire area may be generated.

Therefore, the image processing device 100 performs an image registration process in which a curvature of teeth generated in the oral scan image 300-1 is corrected and then the oral scan image 300-1 is combined with the CT scan image 200.

Figure 7:
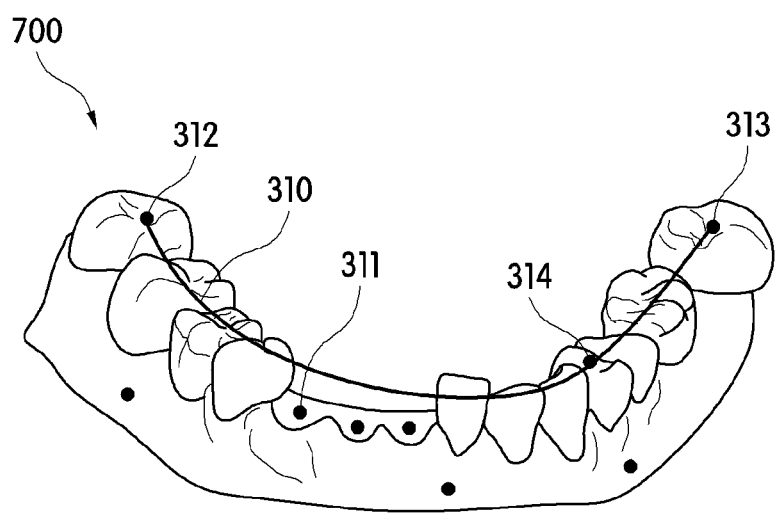
FIG. 7 is a view displaying a mandibular shape in an oral scan image which is input to the image processing device according to an embodiment of the present invention.

For this, in order to check teeth arrangement of the person to be treated, the image processing device 100 may change an angle and a direction of an image in which a structure of the inside of the oral cavity is scanned. FIG. 7 is a view displaying a mandibular shape in an oral scan image which is input to the image processing device according to an embodiment of the present invention.

The CT scan image 200 and the oral scan image 300-1 may be provided as a plurality of images in which the inside of the oral cavity of the person to be treated is captured in various directions or as a three-dimensional image using the plurality of images.

Therefore, the image processing device 100 controls a direction in which the CT scan image 200 and the oral scan image 300-1 are displayed. Then, the image processing device 100 may output an image in a direction required for correction of curvature of teeth of the structure of the inside of the oral cavity of the person to be treated.

First, in order to check mandibular teeth arrangement from the oral scan image 300-1, the image processing device 100 may change a direction (or display direction) of the mandibular shape 23. For example, the image processing device 100 may change a direction of the mandibular shape 23 and display a mandibular shape 700 illustrated in FIG. 7.

The image processing device 100 may check mandibular teeth arrangement 310 on the basis of the displayed mandibular shape 700. For example, the image processing device 100 may determine the mandibular teeth arrangement 310 in the oral scan image on the basis of the arrangement of crowns checked from the mandibular shape 700 and/or at least some of the reference markers 311, 312, 313, and 314 attached to the crowns.

According to various embodiments, the image processing device 100 may change a display direction of a mandibular shape in the CT scan image using a method which is the same as or similar to the above-described method and may determine mandibular teeth arrangement in the CT scan image.

Figure 8:
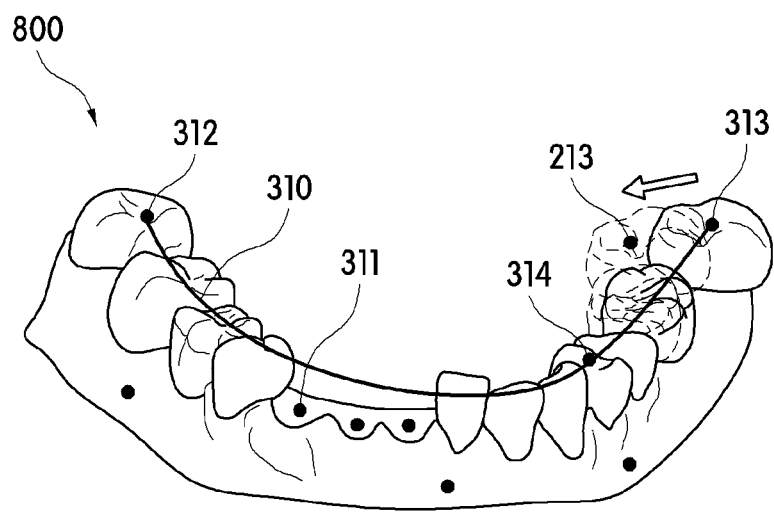
FIG. 8 illustrates a view in which distortion occurred to a shape in an oral scan image which is input to the image processing device according to an embodiment of the present invention is corrected.

The image processing device 100 may compare the determined mandibular teeth arrangement 310 in the oral scan image with the determined mandibular teeth arrangement in the CT scan image and correct the oral scan image in relation to a non-corresponding portion as illustrated in FIG. 8. FIG. 8 illustrates a view in which distortion occurred to a shape in an oral scan image which is input to the image processing device according to an embodiment of the present invention is corrected.

According to an embodiment, the image processing device 100 may compare the mandibular teeth arrangement 310 in the oral scan image with a curvature related to the entire mandibular teeth arrangement in the CT scan image and a curvature related to a portion thereof to check a non-corresponding portion.

The image processing device 100 corrects the oral scan image 700 on the basis of the CT scan image 200 in relation to a portion with a non-corresponding curvature. For example, as illustrated in FIG. 8, the image processing device 100 may determine a portion in which curvatures do not correspond in the CT scan image 200 and the oral scan image 700. In this case, when a reference marker is included in the portion in which the curvatures do not correspond, the image processing device 100 may check corresponding reference markers 213 and 313.

The image processing device 100 may correct the oral scan image 700 so that it matches the shape and curvature of crowns and the location of the reference marker 213 of the CT scan image. For example, the image processing device 100 may distort the images so that the location of the reference marker 313 in the oral scan image 700 corresponds to the location of the reference marker 213 in the CT scan image. In addition, the image processing device 100 may distort the images so that a curvature of a portion in the vicinity of a crown to which the reference marker 313 is attached in the oral scan image 700 corresponds to a curvature of a portion in the vicinity of a crown to which the reference marker 213 is attached in the CT scan image 200 and may generate a corrected oral scan image 800. In this case, the image processing device 100 may control at least some of a proportion, a magnification, and a direction of an image and the arrangement and size of the teeth 30.

When it is checked that the structure of the inside of the oral cavity displayed in the oral scan image matches the structure of the inside of the oral cavity displayed in the CT scan image, the image processing device 100 registers the CT scan image 200 and the corrected oral scan image 800 and generates a registered image. According to an embodiment, when the mandibular shape 23 is corrected as described above, the image processing device 100 may generate aligned oral scan images 21 and 800 which include the image of the maxillary shape 21 and the corrected oral scan image 800 related to the lower jaw in relation to the upper jaw and the lower jaw of the person to be treated.

The image processing device 100 may generate a registered image on the basis of the aligned oral scan images. For example, the image processing device 100 may generate a registered image by matching reference markers included in the aligned oral scan images 21 and 800 and the CT scan image 200.

FIG. 9 illustrates a registered image 900 in which a CT scan image and an oral scan image are registered using the image processing device 100 according to an embodiment of the present invention. The image processing device 100 may check, through the registered image 900, the structure of the inside of the oral cavity checked from the CT scan image 200, the structure of the inside of the oral cavity checked from the oral scan image, a registered structure of the inside of the oral cavity, and teeth arrangement of the person to be treated. The image processing device 100 may generate a teeth profile of the person to be treated on the basis of the generated registered image 900. Here, the teeth profile may include, in relation to the implant placement location 3 and a surrounding area thereof of the person to be treated, images of the structure and shape of an alveolar bone, the shape of gums formed at the alveolar bone, the shapes of roots and crowns of surrounding teeth, and teeth arrangement and information related thereto. Further, the teeth profile may include, in addition to the images and information related to the teeth arrangement, images and/or information related to the shape and size of the inside of the oral cavity.

The image processing device 100 may check, through the teeth profile, pieces of information such as a condition of gum tissues, a bone density of an alveolar bone, a thickness of gums, a thickness of the alveolar bone, and a distance between specific points, in addition to shapes (or outer shapes) related to the inside or the oral cavity or factors inside the oral cavity (e.g., an alveolar bone, a root, and the like).

The image processing device 100 generates a design image of a structure mounted inside the oral cavity for implant surgery for the person to be treated, e.g., a crown or a surgical guide, on the basis of the registered image 900 or the teeth profile.

According to an embodiment, the image processing device 100 may determine a shape of at least one of crowns c1, c2, and c3, which are placed in implant placement locations 3, on the basis of the oral scan images 21 and 800 included in the registered image 900.

For example, when designing the shape of the crown c3, the image processing device 100 may determine an occlusion height with the opposing teeth t on the basis of the aligned oral scan images 21 and 800. The image processing device 100 may determine a height and shape of a masticatory surface of the crown c3 according to the determined occlusion height and the mastication groove of the opposing teeth t displayed in the image of the occlusion alignment variable piece 50.

Likewise, the image processing device 100 may determine shapes of the remaining crowns c1 and c2. The image processing device 100 may arrange the designed crowns c1, c2, and c3 as in the registered image 900. The image processing device 100 may modify the heights or shapes of the crowns in consideration of the arrangement of the crowns c1, c2, and c3 and teeth adjacent thereto.

That is, in processing alignment and registration of the images, the image processing device 100 may calculate a suitable occlusion height in relation to the opposing teeth and manufacture the crowns c1, c2, and c3 accurately and precisely on the basis of the calculated occlusion height. In this way, by minimizing re-design and re-installation of the crowns, the waste of time and cost required for surgery may be minimized, and surgery may be performed efficiently and promptly.

Figure 10:
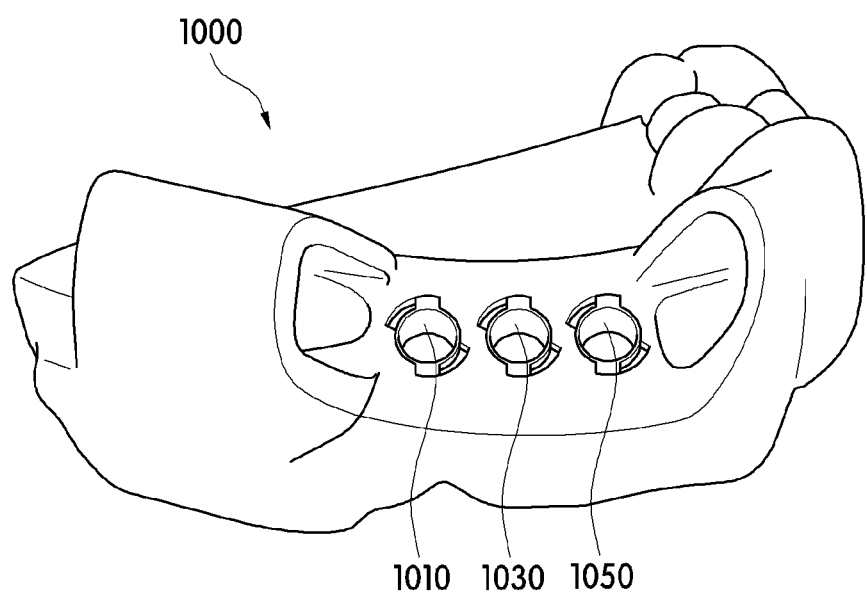
FIG. 10 is a design image of a structure generated on the basis of a registered image or a teeth profile using the image processing device according to an embodiment of the present invention.

In addition, the image processing device 100 may determine information related to placement of an abutment al or a fixture f1 used in implant surgery together with a crown and reflect the determined information to a design image of a structure. FIG. 10 is a design image of a structure generated on the basis of a registered image or a teeth profile using the image processing device 100 according to an embodiment of the present invention.

According to an embodiment, a design image 1000 of a structure may include one or more guide holes 1010, 1030, and 1050 configured to guide drilling for inserting a fixture into an implant placement location 3 inside the oral cavity.

In the design image 1000, shape information of a fixing groove portion whose shape is matched to a surgical guide at an outer profile so as to be matched to at least a portion of an outer profile of the teeth profile displayed in the registered image 900 is set.

For example, the fixing groove portion may be set to correspond to a gum profile of the implant placement location 3 and profiles of crowns and gums around the implant placement location 3 using outer profile information on crowns and gums displayed in the registered image 900 or teeth profile.

In addition, in the design image 1000, location information on the guide holes 1010, 1030, and 1050 is set according to the implant placement locations 3 which are preset in the teeth profile. Here, the guide holes 1010, 1030, and 1050 may be designed to precisely guide a direction and a depth of drilling in supporting a drill and forming a borehole in the alveolar bone of the person to be treated. In addition, the guide holes 1010, 1030, and 1050 are designed to pass through a portion of a surgical guide.

For example, the guide holes 1010, 1030, and 1050 may be set according to directions/diameters of boreholes at portions corresponding to the implant placement locations 3 in the surgical guide. In this case, the directions/diameters of the boreholes may be determined using the shape and bone density of the alveolar bone, a distance from a surrounding root, and the like of the implant placement locations 3 displayed in the registered image. The above-described design information of the guide holes 1010, 1030, and 1050 may be determined in consideration of a state in which the surgical guide is fixed to the inside of the oral cavity through the fixing groove portion and a state in which the drill is supported at the surgical guide.

The image processing device 100 sends the design image to a 3D printer and processes the surgical guide according to the design image 1000 to be printed. The surgical guide formed according to the design image 1000 may guide surgery such as drilling and fixture placement while the surgical guide is fixed to the inside of the oral cavity of the person to be treated.

By registering images on the basis of an improvement in preciseness of image registration and generating a design image of a surgical guide which is designed on the basis of an image registration result as described above, design accuracy may be improved. Therefore, implant surgery including borehole drilling/fixture engagement and the like using the surgical guide may be accurately guided, and safety and completeness of implant surgery may be improved.

Figure 11:
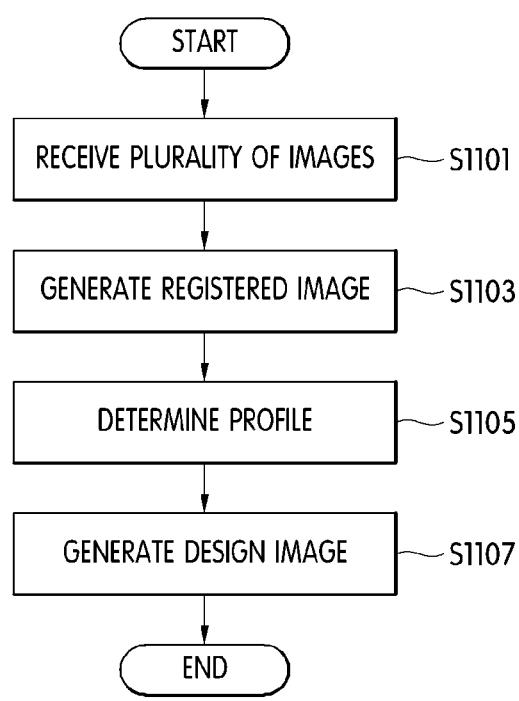
FIG. 11 illustrates a flowchart of an operation in which a design image related to an inside of an oral cavity of a person to be treated is generated using a CT scan image and an oral scan image using the image processing device according to an embodiment of the present invention.

FIG. 11 illustrates a flowchart of an operation in which a design image related to an inside of an oral cavity of a person to be treated is generated using a CT scan image and an oral scan image using the image processing device 100 according to an embodiment of the present invention.

The image processing device 100 receives a plurality of images (S1101). The plurality of images may include a CT scan image and an oral scan image related to an inside of an oral cavity of a person to be treated. Here, the oral scan image may include a separation oral scan image in a state in which an upper jaw and a lower jaw of the person to be treated are separated and an occlusion oral scan image in a state in which the upper jaw and the lower jaw are occluded. The occlusion oral scan image may include an image of a state in which an occlusion alignment variable piece is installed in relation to an implant placement location of the person to be treated.

The image processing device 100 receives a CT scan image and a plurality of oral scan images from at least one external device 130. According to an embodiment, the image processing device 100 may acquire an image from at least one image acquisition device connected thereto via a communication unit 107. For example, at least one of a CT device or an oral scanning device may be provided as the image acquisition device.

The image processing device 100 generates a registered image (S1103). The registered image may be an image generated by registering at least a partial matching area of the CT scan image and the oral scan images. The image processing device 100 may detect a plurality of reference markers from each of the received images, register the images on the basis of the detected reference markers, and generate the registered image.

According to an embodiment, the image processing device 100 may detect reference markers displayed in each of the received CT scan image and oral scan images. In detecting the reference markers, the image processing device 100 may detect the reference markers using a designated shape, a designated color, and a recessed portion formed in a resin structure.

The image processing device 100 may match the images using the plurality of reference markers detected from each of the images and register the images to generate the registered image.

In matching the reference markers, the image processing device 100 may perform an operation for generating a registered image in a state in which the upper jaw and the lower jaw of the person to be treated are occluded. For example, the image processing device 100 may control a maxillary shape and a mandibular shape included in the separation oral scan image to match a maxillary shape and a mandibular shape in the occlusion oral scan image. The image processing device 100 may match the images using the reference markers detected from each of the images.

Here, the image processing device 100 may change (or modify) a portion of the maxillary shape or the mandibular shape. For example, the image processing device 100 may match the images by controlling pieces of information such as curvature of teeths of the maxillary shape or the mandibular shape, magnification of a partial area, and a display direction. In this case, the image processing device 100 may process the images by separating the maxillary shapes and the mandibular shapes included in the images.

For example, when checking images in which curvature of teeths do not correspond to each other, the image processing device 100 may correct a curvature of teeth displayed in the separation oral scan image or the occlusion oral scan image on the basis of a curvature of teeth displayed in the CT scan image.

The image processing device 100 may remove the image of the occlusion alignment variable piece from the occlusion oral scan image which is matched with the separation oral scan image. As described above, the image processing device 100 may generate oral scan images related to the inside of the oral cavity in a state in which the upper jaw and the lower jaw of the person to be treated are occluded. The image processing device 100 may include the generated oral scan images related to the inside of the oral cavity and generate a registered image by registering the CT scan image and the oral scan images related to the inside of the oral cavity.

The image processing device 100 determines a profile (S1105). Here, the profile may include a teeth profile related to the inside of the oral cavity of the person to be treated which is based on the registered image. According to an embodiment, the teeth profile may include shapes related to a surface and an inner portion of a structure of the inside of the oral cavity of the person to be treated. For example, the teeth profile may include at least some of pieces of information related to the size of the inside of the oral cavity, the shape of gums, the shape of an alveolar bone, the shape of teeth arrangement, teeth arrangement, the shape of each tooth, a bone density at an implant placement location, and shapes of opposing teeth related to each implant placement location.

The image processing device 100 generates a design image (S1107). Here, the design image may include a design image of a structure whose shape is matched to the inside of the oral cavity on the basis of a teeth profile related to the inside of the oral cavity of the person to be treated included in the registered image. Here, the structure may include at least one of a crown, an abutment, and a fixture which is placed in an implant placement location. In addition, the structure may include a surgical guide which is installed at an implant placement location to guide formation of a borehole for a fixture.

According to an embodiment, the image processing device 100 may determine a shape of a crown on the basis of a registered image, specifically, a teeth profile of the registered image. For example, the image processing device 100 may check shapes of opposing teeth related to an implant placement location through the teeth profile and determine an occlusion height. The image processing device 100 may determine a height of the crown relative to the occlusion height and determine the shape of the crown in consideration of masticatory motion of the opposing teeth. The image processing device 100 may generate a design image of the crown on the basis of the determined shape and height of the crown.

In addition, the image processing device 100 may generate a design image of a surgical guide on the basis of the registered image. In the registered image, the shape of the crown which is generated corresponding to at least a portion of the implant placement location may be disposed. For example, in the teeth profile of the registered image, a combined image of a fixture, an abutment, and a crown to be placed in the implant placement location may be disposed.

The image processing device 100 may display, on the basis of the location at which the crown is disposed and the shape of the crown, a fixing location of a fixture for fixing the crown on an alveolar bone of the person to be treated. Here, the fixing location of the fixture may include at least one of a direction in which the fixture is placed in the alveolar bone and a depth of a borehole for placing the fixture.

The image processing device 100 may generate a guide hole configured to guide drilling for forming a borehole according to the fixing location of the fixture. The image processing device 100 may generate a design image of a surgical guide so that the shape of the surgical guide is matched to that of an outer surface of the implant placement location of the person to be treated, and the surgical guide includes a guide hole.

In addition, the image processing device 100 may process the generated design image to be sent to a 3D printer through the communication unit 107 and be printed.

Hereinafter, reference markers and a process of forming the reference markers will be described in detail with reference to FIGS. 12 and 13.

According to an embodiment, a reference marker 1 formed inside an oral cavity of a person to be treated may be configured to include a resin structure and a reinforcing adhesive. In this case, the reference marker 1 may be formed using at least one syringe.

Figure 12:
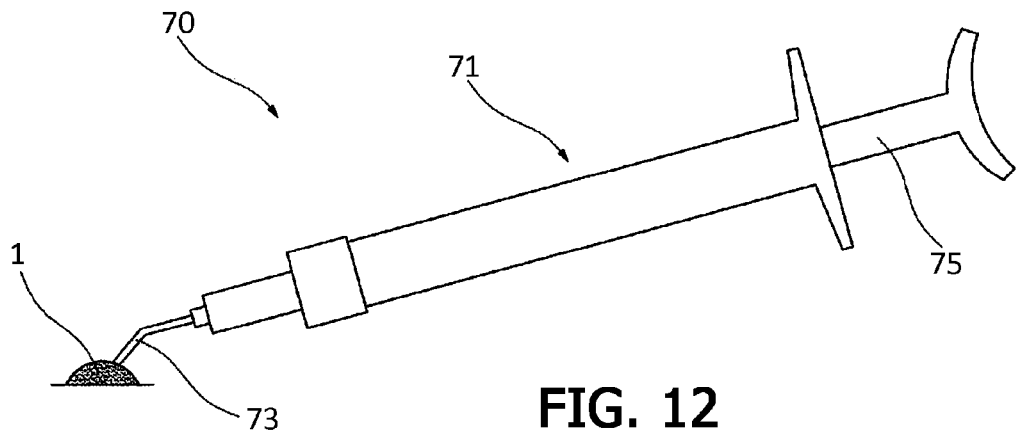
FIG. 12 illustrates a reference marker configured to be attached to an inside of an oral cavity and a syringe configured to discharge the reference marker according to an embodiment of the present invention.

FIG. 12 illustrates a syringe, which discharges a resin adhesive for attachment to the inside of the oral cavity, and the discharged resin adhesive according to an embodiment of the present invention.

According to an embodiment, the resin structure of the reference marker 1 is formed by hardening of the discharged resin adhesive. A first syringe 70 configured to discharge the resin adhesive includes a body 71, a tip portion 73, and a pushrod 75. Here, a filling space which is filled with the resin adhesive is formed in the body 71.

The tip portion 73 is disposed at one side of the body 71 and has an opening which is in communication with the filling space. In addition, the pushrod 75 is coupled to the other side of the body 71 in order to push the resin adhesive filled in the filling space toward the opening of the tip portion 73 and is inserted in one side direction.

In this case, the first syringe 70 presses the pushrod 75 at an implant placement location 3 so that the filled resin adhesive is discharged through the tip portion 73. That is, as the tip portion 73 of the first syringe 70 is disposed at a surface side of teeth 30 and gums 40 and then the pushrod 75 is pressed, the resin adhesive may be discharged and attached to the inside of the oral cavity of the person to be treated.

Meanwhile, in the process of forming the reference marker 1 using the reference adhesive, a reinforcing adhesive layer using a reinforcing adhesive may be formed so that the resin adhesive is promptly hardened even in a humid environment of the inside of the oral cavity, is firmly attached to the inside of the oral cavity of the person to be treated, and forms the resin structure.

According to an embodiment, a tip portion of a syringe (a second syringe) which is filled with the reinforcing adhesive may be disposed at an edge side of the resin adhesive, which is adhered in a semi-spherical shape to the inside of the oral cavity, so that the reinforcing adhesive is discharged. Here, preferably, it should be understood that the structure of the second syringe substantially corresponds to the first syringe 70 and that the first syringe and the second syringe are classified according to a filling material with which the internal filling space is filled.

In this case, the syringes each filled with the resin adhesive and the reinforcing adhesive allow a discharge amount of the resin adhesive and the reinforcing adhesive to be visually checked through scales marked on the bodies of the syringes. Alternatively, a discharge amount upon one pressing of each syringe may also be adjusted to correspond to a designated volume ratio.

In addition, each syringe may be configured so that the pushrod is pressed toward the inside of the body. According to circumstances, the body may be formed of a flexible synthetic resin material, and as the body is pressed, each adhesive may be discharged through the tip portion which protrudes and extends from one side.

Hereinafter, an embodiment of the resin structure and the reinforcing adhesive which constitute the reference marker 1 will be described in detail.

The resin structure may refer to a hardened resin adhesive that is discharged in a designated form. Here, a bionic adhesive used in dental surgery may be provided as the resin adhesive. For example, an adhesive which is harmless to the human body, has a viscosity of a certain value or higher in a hardened state, and may be stably hardened within a range of humidity inside the oral cavity may be provided as the resin adhesive.

According to an embodiment, the resin adhesive may be configured to include at least some of a base mixture, an adhesive monomer, a hydrophilic monomer, an optical initiator, and a diluting solvent. More specifically, the resin adhesive may be configured to include 1 to 55 parts by weight of the base mixture, 1 to 25 parts by weight of the adhesive monomer, 1 to 15 parts by weight of the hydrophilic monomer, 0.1 to 15 parts by weight of the optical initiator, and 10 to 65 parts by weight of the diluting solvent.

According to an embodiment of the base mixture, the base mixture may be provided by mixing, to Bisphenol A glycidyl methacrylate (Bis-GMA), at least one of Tri-GMA and Tetra-GMA.

In this case, when the amount of base mixture is less than 1 part by weight, radiopaqueness is degraded, and a reference marker is unable to be clearly displayed in a CT scan image. On the other hand, when the amount of base mixture exceeds 55 parts by weight, a shape of a resin adhesive which is initially adhered to the inside of the oral cavity is distorted due to excessive viscosity, and it is difficult to recognize the resin adhesive as a registration point for image registration.

For example, when the resin adhesive is attached to the inside of the oral cavity of the person to be treated, the surface of the resin adhesive, excluding a portion adhered to the inside of the oral cavity, is formed to be rounded and have a semi-spherical shape as a whole so that surface tension is minimized. In this case, when the viscosity of the resin adhesive is excessive, since the resin adhesive is unable to be formed in the semi-spherical shape as described above, its function as a standard for image registration may be degraded.

Therefore, the base mixture of the resin adhesive may be mixed by 1 to 55 parts by weight so that the hardened resin adhesive stably forms the semi-spherical shape which is clearly displayed in a CT scan image.

According to an embodiment of the adhesive monomer, the adhesive monomer may be configured to include carboxylic acid and derivatives thereof and functional groups such as a phosphoric acid group and a sulfonic acid group.

For example, the adhesive monomer may be one of a monocarboxylic acid, dicarboxylic acid, tricarboxylic acid, (meth)acrylic acid, maleic acid, p-vinylbenzoic acid, 11-(meth)acryloxy-1,1-undecanedicarboxylic acid, 1,4-di (meth)acryloyloxyethyl pyromellitic acid, an additive of 2-hydroxyethyl (meth)acrylate and pyromellitic dianhydride (PMDM), 2-(meth)acryloyloxyethyl phosphate, and 2- and 3-(meth)acryloyloxypropyl phosphate or a mixture of two or more thereof.

In this case, a predetermined adhesive force is formed by mixing the adhesive monomer. Therefore, the adhesive monomer may minimize mobility of the resin adhesive, which is discharged in a semi-spherical shape to the inside of the oral cavity, due to the weight and viscosity.

In addition, according to an embodiment of the hydrophilic monomer, the hydrophilic monomer may be hydroxyethyl methacrylate or hydroxypropyl methacrylate (HPMA) and has an effect of improving an adhesive force in a humid condition inside the oral cavity.

When the amount of the hydrophilic monomer is less than 1 part by weight, the effect thereof may be insufficient, and when the amount of the hydrophilic monomer exceeds 15 parts by weight, an adhesive force may be degraded due to excessive hydrophilicity.

According to an embodiment of the optical initiator, the optical initiator may be camphorquinone (CQ) or the like. In addition, the optical initiator may be configured to include a reducing agent such as N, N-dimethylaminoethyl methacrylate (DMAEMA) or ethyl p-dimethylamino benzoate (EDMAB).

When the amount of optical initiator is 0.1 part by weight, due to degradation of a polymerization speed, movement of the oral cavity of the person to be treated may occur. In addition, due to movement or deformation of the resin adhesive during image scanning, image accuracy of the reference marker 1 displayed in the scanned image may also be degraded. When the amount of optical initiator exceeds 15 parts by weight, there is a concern that the monomer may not be polymerized to a single monomer and thus an adhesive strength may be degraded.

According to an embodiment, the optical initiator included in the resin adhesive may harden the resin adhesive using light in a specific wavelength range through a photopolymerizer which will be described below.

Further, according to an embodiment of the diluting solvent, the diluting solvent may be water, ethyl alcohol, acetone, and the like, and more preferably, may be formed of a material with high volatility for removing moisture inside the oral cavity. A water film between the resin adhesive and a surface of the inside of the oral cavity may be removed by the diluting solvent, and an adhesive force of the resin adhesive may be significantly improved.

Figure 13:
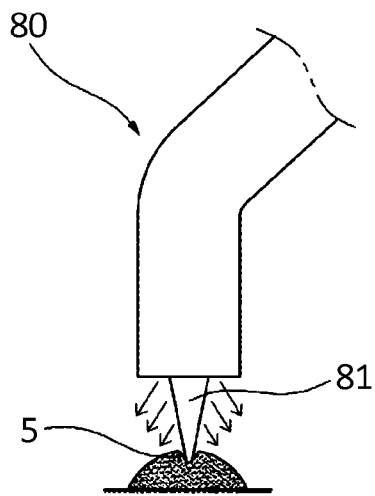
FIG. 13 illustrates a reference marker configured to be attached to an inside of an oral cavity and a photopolymerizer configured to harden the reference marker according to an embodiment of the present invention.

Meanwhile, the resin adhesive attached to the inside of the oral cavity of the person to be treated may be hardened by a photopolymerizer 80 and form the resin structure as illustrated in FIG. 13. FIG. 13 illustrates a reference marker configured to be attached to an inside of an oral cavity and a photopolymerizer configured to harden the reference marker according to an embodiment of the present invention.

According to an embodiment, a wedge portion 81 configured to press a surface of the resin adhesive is disposed at an end of the photopolymerizer 80. The wedge portion 81 may press a surface of the resin adhesive and form a recessed portion 5, which has the shape of the wedge portion 81, that comes into contact with the resin adhesive.

A wavelength of light irradiated from the photopolymerizer 80 may be differently set according to a type of an optical initiator included in the resin adhesive. For example, when the resin adhesive is a visible light hardening type, light irradiated from the photopolymerizer 80 may be set to have a visible light wavelength. In addition, when the resin adhesive is an ultraviolet (UV) light hardening type, the irradiated light may be set to have a UV wavelength, and when the resin adhesive is an infrared (IR) light hardening type, the irradiated light may be set to have an IR wavelength.

Here, the wedge portion 81 may be formed of a transparent or semi-transparent material through which a light source emitted from the photopolymerizer 80 may be transmitted. The wedge portion 81 may have a narrow and sharp shape whose area decreases toward an end, e.g., a conical shape.

In the state in which the recessed portion 5 is formed by the wedge portion 81 pressing a surface of the resin adhesive, light irradiated by being transmitted through the photopolymerizer 80 and the wedge portion 81 hardens the resin adhesive, and attachment of the resin adhesive through the reinforcing adhesive layer and a fixing force of the formed resin structure may be further improved using a pressing force that causes the recessed portion 5 to be formed.

Here, the formed recessed portion 5 may be displayed to be darker than its surroundings according to a density, an amount of reflected light, and the like in an oral scan image and a CT scan image. In this way, the image processing device 100 may detect the recessed portion 5 formed in the resin structure in the image registration process of the oral scan image and the CT scan image and detect the reference markers 1 displayed in the images on the basis of the recessed portion 5. The image processing device 100 may determine at least some of the detected reference markers 1 as registration points.

According to an embodiment, the reinforcing adhesive may be a liquid including a cyanoacrylate monomer.

Here, the reinforcing adhesive may be configured to include alkyl cyanoacrylate such as N-butyl-2-cyanoacrylate, ethyl-2-cyanoacrylate, and 2-octyl-cyanoacrylate.

For example, Histoacryl, which is a bionic adhesive having N-butyl-2-cyanoacrylate as a main component, or Dermabond, which is a bionic adhesive having octyl-2-cyanoacrylate as a main component, may be used as the reinforcing adhesive.

Since the reinforcing adhesive is provided substantially as a liquid, the reinforcing adhesive may permeate into a gap between a surface of the inside of the oral cavity and the resin adhesive and be promptly hardened. Therefore, since the reinforcing adhesive is hardened in an instant and fixed to the inside of the oral cavity while the resin adhesive is being hardened, the resin structure may be prevented from being separated or detached from the inside of the oral cavity during acquisition of a CT image and an oral scan image.

Further, the reinforcing adhesive, which is provided as a liquid, may easily permeate into a fine gap between the surface of the inside of the oral cavity and the resin adhesive. Therefore, since the reinforcing adhesive is formed in the form of a thin film, the resin structure may be fixed in a state of substantially being adhered to the inside of the oral cavity, and locations of registration points for image registration may be clearly displayed inside the oral cavity.

In addition, since the reinforcing adhesive further includes a paint of a preset color, a portion at which the reinforcing adhesive is discharged and formed may be clearly visually differentiated from other portions. Therefore, convenience of surgery performed by an operator may be significantly improved.

In addition, the reinforcing adhesive may be provided as a component which is biodegraded inside the oral cavity while having a stronger adhesive property than the resin adhesive and a property of being more promptly hardened than the resin adhesive.

For example, the reinforcing adhesive may further include a protein component which is effective to a bionic adhesive and a biodegradable polymer material capable of degrading the protein component. According to an embodiment, since the reinforcing adhesive includes components such as lactide and caprolacton, the reinforcing adhesive is naturally biodegraded and removed even when the reinforcing adhesive is adhered to a portion inside the oral cavity. In this way, inconvenience of a person to be treated may be minimized.

Further, since the resin adhesive may be promptly and firmly fixed by the reinforcing adhesive even when the resin adhesive is formed on a surface of at least one of gums, teeth, and metal prostheses inside the oral cavity, the reliability of image registration using the images in which the reference markers are displayed may be significantly enhanced.

Inside the oral cavity of the person to be treated, the resin adhesive and the reinforcing adhesive may be discharged by a designated volume ratio and form the reference markers 1. According to an embodiment, it is preferable that the resin adhesive and the reinforcing adhesive be discharged at a volume ratio in the range of 1:0.05 to 1:0.2.

TABLE 1

| Reinforcing adhesive | Less than 0.05 | 0.05 to 0.2 | Greater than 0.2 |
|---|---|---|---|
| Adhesive force | Failure (separation of resin registration portion) | Fine | Fine (difficult to separate resin registration portion) |

Meanwhile, Table 1 is a table showing adhesive forces according to volume ratios of the resin adhesive to the discharged reinforcing adhesive. Here, the adhesive force test in Table 1 was conducted by discharging the same amount of resin adhesive to a plurality of sites on a surface of a test piece which was prepared to have a humidity level and a temperature similar to those of the inside of the oral cavity, discharging the reinforcing adhesive in the conditions shown in Table 1, and then observing, by visual inspection, adhesion states of the resin adhesives according to an external impact and vibration.

As shown in Table 1, when the resin adhesive and the reinforcing adhesive are discharged at a volume ratio less than 1:0.05, the adhesive force may be degraded, and the resin adhesive may be easily separated from the test piece due to an external impact and vibration.

In addition, when the resin adhesive and the reinforcing adhesive are discharged at a volume ratio which exceeds 1:0.2, the adhesive force is fine, but it is difficult to separate the resin adhesive from the test piece after the test. In addition, since an amount of the reinforcing adhesive being used unnecessarily increases, it is not economically feasible. Therefore, when the reinforcing adhesive forming the reinforcing adhesive layer with respect to the resin adhesive is discharged at the volume ratio in the range of 1:0.05 to 1:0.2, the resin adhesive may be formed to have a fixing force that allows the resin adhesive to be naturally removed when a predetermined force is applied thereto after image acquisition while separation or movement of the resin adhesive is prevented. Therefore, preciseness may be significantly improved during image registration using a CT scan image and an oral scan image. Here, it is preferable that the predetermined force be understood as a force larger than a force generated due to general movement inside the oral cavity.

Meanwhile, various embodiments of the present invention disclosed in the present specification and the drawings are merely intended to facilitate description of technical contents of the present invention and propose specific examples to assist understanding of the present invention and are not intended to limit the scope of the present invention.

That is, it should be apparent to those of ordinary skill in the art to which the present invention pertains that other modified examples based on the technical idea of the present invention may be practiced.

The invention claimed is:

1. A method for processing an image for generating a design image based on a reference marker, the method comprising:
   receiving, from at least one external device, images related to a person to be treated who has a plurality of reference markers attached to an inside of an oral cavity, the images including a computerized tomography (CT) scan image and a plurality of oral scan images;
   generating a registered image by registering the images on basis of locations of the plurality of reference markers detected from the images;

determining, on basis of the registered image, a teeth profile related to the inside of the oral cavity of the person to be treated; and generating a design image related to the inside of the oral cavity on basis of the teeth profile, wherein the generating of the registered image includes: correcting a curvature of teeth included in the oral scan images, on basis of at least part of the plurality of reference markers, the teeth profile, and a curvature of teeth included in the CT scan image.

2. The method of claim 1, wherein the plurality of oral scan images include; a separation oral scan image related to a state in which an upper jaw and a lower jaw are separated prior to installation of an occlusion alignment variable piece; and an occlusion oral scan image related to a state in which the upper jaw and the lower jaw are occluded after the installation of the occlusion alignment variable piece.

3. The method of claim 2, wherein:
the design image includes an image of a structure whose shape is matched to that of the inside of the oral cavity; and
the shape of the structure includes a fixing groove portion whose shape is matched to at least a portion of the teeth profile and a guide hole configured to guide drilling at a preset implant placement location.

4. The method of claim 2, wherein the generating of the registered image further includes: controlling, on basis of the locations of the plurality of reference markers, a maxillary shape and a mandibular shape in the separation oral scan image to match a maxillary shape and a mandibular shape in the occlusion oral scan image.

5. The method of claim 4, wherein:
the design image includes an image of a crown to be placed in an implant placement location of the person to be treated; and
a shape of the crown is determined on basis of shapes of opposing teeth related to the placement location which are confirmed from the registered image.

6. The method of claim 5, wherein the design image includes information on a placement location of a fixture, to which the crown is fixed, which is determined on basis of a state in which the image of the crown is disposed at the placement location in the registered image.

7. A device for processing an image for generating a design image based on a reference marker, the device comprising:
a communication unit configured to receive, from at least one external device, images related to a person to be treated who has a plurality of reference markers attached to an inside of an oral cavity, the images including a computerized tomography (CT) scan image and a plurality of oral scan images; and
a processor configured to generate a registered image by registering the received images on basis of locations of the plurality of reference markers detected from the images and configured to generate a design image of the inside of the oral cavity according to a teeth profile related to the inside of the oral cavity of the person to be treated which is determined on basis of the registered image,
wherein the processor is further configured to correct a curvature of teeth included in the oral scan image on basis of at least part of the plurality of reference markers, the teeth profile, and a curvature of teeth included in the CT scan image.

8. The device of claim 7, wherein the plurality of oral scan images include: a separation oral scan image related to a state in which an upper jaw and a lower jaw are separated prior to installation of an occlusion alignment variable piece; and an occlusion oral scan image related to a state in which the upper jaw and the lower jaw are occluded after the installation of the occlusion alignment variable piece.

9. The device of claim 8, wherein the processor is configured to generate the registered image by controlling, on basis of the locations of the plurality of reference markers detected from the images, a maxillary shape and a mandibular shape in the separation oral scan image to match a maxillary shape and a mandibular shape in the occlusion oral scan image.

10. The device of claim 9, wherein:
the design image includes an image of a crown to be placed in an implant placement location of the person to be treated; and
the processor is configured to determine a shape of the crown on the basis of shapes of opposing teeth related to the placement location which are confirmed from the registered image.

11. The device of claim 10, wherein the processor is configured to determine information on a placement location of a fixture, to which the crown is fixed, on the basis of a state in which the image of the crown is disposed at the placement location in the registered image and causes the information on the placement location of the fixture to be included in the design image.

12. The device of claim 7, wherein:
the design image includes an image of a structure whose shape is matched to that of the inside of the oral cavity; and
the processor is configured to determine the shape of the structure to include a fixing groove portion whose shape is matched to at least a portion of the teeth profile and a guide hole configured to guide drilling at a preset implant placement location.

13. A device for processing an image for generating a design image based on a reference marker, the device comprising:
a communication unit configured to receive, from at least one external device, images related to a person to be treated who has a plurality of reference markers attached to an inside of an oral cavity, the images including a computerized tomography (CT) scan image and a plurality of oral scan images; and
a processor configured to generate a registered image by registering the received images on basis of locations of the plurality of reference markers detected from the images and configured to generate a design image of the inside of the oral cavity according to a teeth profile related to the inside of the oral cavity of the person to be treated which is determined on basis of the registered image,
wherein the plurality of oral scan images include: a separation oral scan image related to a state in which an upper jaw and a lower jaw are separated prior to installation of an occlusion alignment variable piece; and an occlusion oral scan image related to a state in which the upper jaw and the lower jaw are occluded after the installation of the occlusion alignment variable piece, and
wherein the processor is configured to generate the registered image by controlling, on basis of the locations of the plurality of reference markers detected from the images, a maxillary shape and a mandibular shape in the separation oral scan image to match a maxillary shape and a mandibular shape in the occlusion oral scan image.

14. The device of claim 13, wherein:
the design image includes an image of a crown to be placed in an implant placement location of the person to be treated; and
the processor is configured to determine a shape of the crown on the basis of shapes of opposing teeth related to the placement location which are confirmed from the registered image.

15. The device of claim 14, wherein the processor is configured to determine information on a placement location of a fixture, to which the crown is fixed, on the basis of a state in which the image of the crown is disposed at the placement location in the registered image and causes the information on the placement location of the fixture to be included in the design image.

* * * * *